United States Patent [19]
Hölderich et al.

[11] Patent Number: 6,051,706
[45] Date of Patent: Apr. 18, 2000

[54] METHOD OF PRODUCING ε-CAPROLACTAM

[75] Inventors: Wolfgang Hölderich, Frankenthal; Georg Philip Heitmann, Heinsberg, both of Germany; Dietrich Arntz, Mobile, Ala.

[73] Assignee: Degussa-Hüls Aktiengesellschaft, Frankfurt, Germany

[21] Appl. No.: 09/309,506

[22] Filed: May 11, 1999

[30] Foreign Application Priority Data

May 14, 1998 [DE] Germany .................... 198 21 700

[51] Int. Cl.[7] ................................................. C07D 201/04
[52] U.S. Cl. ............................................................ 540/536
[58] Field of Search ................................................ 540/536

[56] References Cited

U.S. PATENT DOCUMENTS

| | | | |
|---|---|---|---|
| 4,717,769 | 1/1988 | Sato et al. ................................. | 540/536 |
| 5,741,904 | 4/1998 | Hoelderich et al. ..................... | 540/536 |

FOREIGN PATENT DOCUMENTS

| | | |
|---|---|---|
| 9-241236 | 9/1997 | Japan . |
| 9-241237 | 9/1997 | Japan . |

OTHER PUBLICATIONS

Yashima (Catal. Today (1997), 38(2), 249–253); 1997.
Dai et al. (Chem. Commun., 1996, 1071–1072), 1996.
Roseler et al. (Stud. Surf. Sci. Catal. (1997), 105B "Progress in Zeolite and Microporous Materials", Pt. B), 1173–1180), 1997.
Roeseler et al. (Appl. Cata., A (1996), 144 (1–2), 319–333), 1996.
Holderich et al. (Catalysis Today 37 (1997) 353–366, 1997.

*Primary Examiner*—Mukund J. Shah
*Assistant Examiner*—Bruck Kifle
*Attorney, Agent, or Firm*—Smith, Gambrell & Russell, LLP

[57] ABSTRACT

A method is disclosed of producing ε-caprolactam by the Beckmann rearrangement of cyclohexanone oxime using (B) β zeolites as catalyst.

3 Claims, No Drawings

000
METHOD OF PRODUCING ε-CAPROLACTAM

INTRODUCTION AND BACKGROUND

The present invention relates to an improved method of producing ε-caprolactam from cyclohexanone oxime in the gaseous phase using (B) β-zeolites.

It is known that ε-Caprolactam is of great economic significance as the starting point for the synthesis of Nylon 6. In the classic production method primarily used today, cyclohexanone oxime is reacted in the presence of fuming sulfuric acid by way of the well known Beckmann rearrangement to form ε-caprolactam. A disadvantage of this method is the use of ammonia which is necessary for the neutralization of the sulfuric acid and which is associated with an accumulation of ammonium sulfate of up to 4.5 t per t caprolactam. In order to avoid this undesired byproduct, efforts have been made since the middle of the sixties to carry out the reaction with the aid of heterogeneous catalysis.

It is known that ε-caprolactam can be produced from cyclohexanone oxime in the gaseous phase on solid catalysts, e.g., on zeolites having an MFI structure.

However, X and Y zeolites and mordenites in the H form or doped with rare earth metals or transition metals deactivate extremely rapidly. 5-Cyanopent-1-ene, cyclohexane and cyclohexanol are extensively formed in the presence of these catalysts as byproducts. Efforts have been made to avoid the known problems. Temperatures below 400° C. atmospheric pressure were suggested as process parameters. Furthermore, non-polar solvents such as cyclohexane, benzene or toluene are supposed to be more advantageous than the use of more polar solvents. The partial blocking of the acidic centers of the HY zeolite with Na did not result in an improvement of the results (M. Burquet et al., An. Quim. Ser. A 81 (1985) 259; A. Aucejo et al., Appl. Catal. 22 (1986) 187 and A. Corma et al., Zeolites 11 (1991) 593). However, the authors determined that strongly acidic Brønstedt acid centers with $pKa \leq 1.5$ are necessary for the Beckmann rearrangement and that the selectivity-reducing byproduct 5-cyanopent-1-ene is formed both on the acidic centers as well as on the $Na^+$ ions. Furthermore, the authors surmise that the deactivation of the zeolite catalyst takes place as a result of basic byproducts such as aniline and methyl pyridine and not by the formation of coke on the catalytic surface since the color of the catalyst is still almost white after the reaction.

In order to avoid the disadvantages of the rapid ageing of the X- and Y zeolite catalysts, pentasil zeolites (MFI structure) were extensively investigated.

Zeolites with MFI structure are also regarded as favorable in the patents EP 0,494,535 and EP 0,544,530. However, a high Si/M ratio of 5 to 500 is required for these materials, wherein the metal can be Al, B, and Ga, among others. Alcohols and ethers as well as water are mentioned as added components. The maximum addition of water is approximately 0.06–2.5 moles per mole oxime.

The experiments for improving the service life of the catalyst also went in the direction that the outer surface of a boron-MFI zeolite was covered with Na ions in order to neutralize the acidity on the outer surface in this manner (EP 0,086,543 (May 17, 1986) Stamicarbon). A mixture of cyclohexanone oxime, toluene, carbon dioxide and water in a molar ratio of 1:3:7 at 340° C. will react the cyclohexanone oxime quantitatively on this catalyst. The selectivity for ε-caprolactam is indicated as 58%.

It is also known that β zeolites can be used in this reaction. However, the ε-caprolactam is produced only with a selectivity of 86.9% at a conversion of 80.6% (C.A. 127:278 152, JP-OS 97 241 237).

It is therefore an object of this invention to improve the method of producing ε-caprolactam by the Beckmann rearrangement in the gaseous phase with the aid of other catalysts.

SUMMARY OF THE INVENTION

The above and other object s may be achieved according to the present invention by carrying out the Beckmann rearrangement of cyclohexanone oxime in the gaseous phase in a temperature range of 250 to 450° C. in the presence of zeolite catalysts which are (B) β zeolites to thereby produce ε-caprolactam.

(A1) β zeolites are known from the state of the art and are commercially available. In order to produce the (B) β zeolite an aqueous mixture of $H_3BO_3$, alkali hydroxide, a silicon component, preferably fine, optionally precipitated silica is mixed together with an amine solution, especially tetraethyl ammonium hydroxide and/or -bromide at 100 to 200° C. in an autoclave under autogenous pressure.

Instead of an aqueous amine solution, an ethereal solution, e.g., with diethyleneglycoldimethylether, or an alcoholic solution, e.g., with 1.6 hexane diol as solvent can be used in this reaction.

Following washing and drying, the obtained crystals are subjected in general to an ammonia stream at temperatures of up to 400° C. for drying and then converted to the ammonium form.

After the calcination at up to 400° C., the zeolite is present in the $H^+$ form and is subsequently additionally subjected to a temperature treatment at 500 to 600° C., preferably 500 to 550° C.

The molecular sieves produced in this manner can be subsequently shaped, if necessary, into strands, tablets or other customary catalytic pellets using a binder. Such procedures are known in the art.

The desired forms for the zeolites are largely a function of the type of reactor intended. It turns out that selectivities of 92% and more can be achieved at the customary reaction temperatures, especially at 300 to 350° C.

DETAILED EMBODIMENTS OF INVENTION

1. Production of the (B) β zeolite 183.64 g $H_2O$, 3.48 g $H_3BO_3$, 1.43 g NaOH, 26.58 g precipitated silica ($SiO_2$ FK-700 Degussa) and 27.20 g of an aqueous tetraethyl ammonium hydroxide solution (40% by weight) are agitated overnight.

31.90 g tetraethyl ammonium bromide are subsequently added and the gel agitated another 5 hours.

This mixture is then maintained in an autoclave for 240 hours under autogenous pressure at 150° C.

After the separation, washing and drying of the crystalline product produced, the calcination takes place in a current of ammonia under a gradual heating up to 400° C. Following this, the zeolite is subjected to an ion exchange with an ammonium chloride solution (1 molar, zeolite 10% by weight) at room temperature.

The subsequent calcination at 400° C. in a current of nitrogen results in the formation of (B) β zeolite in the proton form. Before the latter is used as catalyst a further treatment takes place at 550° C. in an atmosphere of air.

Carrying out of the Beckmann Rearrangement

The experiments are carried out in a stainless steel fixed-bed reactor 10 mm in diameter.

The charging with 1.5 g of the catalyst results in a bed height of approximately 40 mm.

The cyclohexanone oxime used is evaporated dissolved in ethanol (weight ratio 1:9), then vaporized and fed into the reactor in a current of nitrogen carrier gas. The reaction temperatures are 300° C., 100 mbar and 350° C., 1 bar at a WHSV of 0.33 g (reactant) 9cat$^{-1}$h$^{-1}$.

Results

Selectivities between 92 and 97% are obtained according to the invention as described herein.

Further variations and modifications of the foregoing will be apparent to those skilled in the art and are intended to be encompassed by the claims appended hereto.

German priority application 198 21 700.5 is relied on and incorporated herein by reference.

We claim:

1. A method of producing ε-caprolactam, comprising:
   carrying out a Beckmann rearrangement of cyclohexanone oxime in the gaseous phase at a temperature of reaction in the range of 250° to 450° C. in the presence of a (B) β zeolite as a catalyst.

2. The method according to claim 1, wherein the cyclohexanone oxime in the gaseous phase is obtained by dissolving the cyclohexanone oxime in ethanol, vaporizing the resulting solution, and feeding the cyclohexanone oxime in the gaseous phase into a reactor in a current of nitrogen carrier gas.

3. The method according to claim 2 wherein the temperature of reaction is 300° C. at 100 mbar, followed by 350° C. at 1 bar, with a WHSV of 0.33 g, reactant, 9 cat$^{-1}$h$^{-1}$.

* * * * *